United States Patent
Kahra et al.

(10) Patent No.: US 10,675,183 B2
(45) Date of Patent: Jun. 9, 2020

(54) CREATING CUTS IN A TRANSPARENT MATERIAL USING OPTICAL RADIATION

(71) Applicant: Carl Zeiss Meditec AG, Jena (DE)

(72) Inventors: Steffen Kahra, Kunreuth (DE); Herrn Jürgen Kühnert, Jena (DE); Michael Bergt, Weimar (DE)

(73) Assignee: Carl Zeiss Meditec AG, Jena (DE)

( * ) Notice: Subject to any disclaimer, the term of this patent is extended or adjusted under 35 U.S.C. 154(b) by 296 days.

(21) Appl. No.: 15/515,473

(22) PCT Filed: Sep. 29, 2015

(86) PCT No.: PCT/EP2015/072446
§ 371 (c)(1),
(2) Date: Mar. 29, 2017

(87) PCT Pub. No.: WO2016/050779
PCT Pub. Date: Apr. 7, 2016

(65) Prior Publication Data
US 2017/0266047 A1    Sep. 21, 2017

(30) Foreign Application Priority Data

Sep. 29, 2014  (DE) .......... 10 2014 014 565
Sep. 29, 2014  (DE) .......... 10 2014 014 567

(51) Int. Cl.
*A61F 9/008*    (2006.01)

(52) U.S. Cl.
CPC .. *A61F 9/00825* (2013.01); *A61F 2009/0087* (2013.01); *A61F 2009/00872* (2013.01); *A61F 2009/00887* (2013.01); *A61F 2009/00897* (2013.01)

(58) Field of Classification Search
CPC ........ A61F 9/00825; A61F 2009/00897; A61F 2009/00887; A61F 2009/0087; A61F 2009/00872
See application file for complete search history.

(56) References Cited

U.S. PATENT DOCUMENTS 5,549,632 A      8/1996  Lai
2006/0217688 A1*  9/2006  Lai ..................... A61F 9/00804
                                                         606/4

(Continued)

FOREIGN PATENT DOCUMENTS

DE           695 00 997 T2     4/1998
DE      10 2008 027 358 A1    12/2009

(Continued)

OTHER PUBLICATIONS

Merriam-Webster, "Superimpose", https://www.merriam-webster.com/dictionary/superimposed, viewed on Jul. 10, 2019.*

(Continued)

*Primary Examiner* — Christopher Koharski
*Assistant Examiner* — James Moss
(74) *Attorney, Agent, or Firm* — Patterson Thuente Pedersen, P.A.

(57) ABSTRACT

A method for creating cuts in a transparent material using optical radiation, the optical radiation being focused onto the material in a focal point and the focal point being shifted along a curve: A simple or double harmonic curve is used when seen at a right angle to a main direction of incidence of the radiation and preferably successively traveled curves do not lie on top of each other.

20 Claims, 8 Drawing Sheets

(56) References Cited

U.S. PATENT DOCUMENTS

| | | | | |
|---|---|---|---|---|
| 2007/0293851 | A1* | 12/2007 | Muhlhoff | A61F 9/008 606/11 |
| 2008/0077121 | A1* | 3/2008 | Rathjen | A61F 9/00827 606/5 |
| 2011/0251601 | A1* | 10/2011 | Bissmann | A61F 9/00831 606/5 |
| 2011/0264081 | A1* | 10/2011 | Reich | A61B 3/1173 606/4 |
| 2012/0016352 | A1* | 1/2012 | Dick | A61F 9/008 606/5 |
| 2012/0029492 | A1 | 2/2012 | Rathjen | |
| 2014/0330260 | A1* | 11/2014 | Bergt | B23K 26/38 606/5 |

FOREIGN PATENT DOCUMENTS

| | | |
|---|---|---|
| DE | 10 2011 085 047 A1 | 4/2013 |
| DE | 102011085047 A1 * | 4/2013 ............. B23K 26/38 |
| EP | 1 159 986 A2 | 12/2001 |
| WO | WO 2007/042190 A2 | 4/2007 |

OTHER PUBLICATIONS

PCT International Search Report and Written Opinion for International Application No. PCT/EP2015/072446, dated Dec. 5, 2015, 13 pages.

English translation of PCT International Search Report for International Application No. PCT/EP2015/072446, dated Dec. 2015, 2 pages.

DE Search Report for DE 10 2014 014 565.4, dated Jun. 15, 2015, 10 pages.

DE Search Report for DE 10 2014 014 567.0, dated Jun. 22, 2015, 8 pages.

English translation of PCT International Preliminary Report on Patentability and Written Opinion for International Application No. PCT/EP2015/072446, dated Apr. 13, 2017, 11 pages.

English translation of PCT International Preliminary Report on Patentability for International Application No. PCT/EP2015/072295, dated Apr. 13, 2017, 10 pages.

* cited by examiner

CREATING CUTS IN A TRANSPARENT MATERIAL USING OPTICAL RADIATION

RELATED APPLICATIONS

This application is a National Phase entry of PCT Application No. PCT/EP2015/0724446 filed Sep. 29, 2015 which application claims the benefit of priority to German Application No. 10 2014 014 567.0, filed Sep. 29, 2014, and which claims the benefit of priority to German Application No. 10 2014 014 565.4, filed Sep. 29, 2014, the entire disclosures of which are incorporated herein by reference.

FIELD OF THE INVENTION

The invention relates to a method for creating cuts in a transparent material by application of optical radiation, wherein the optical radiation is focused on a focus in the material and the focus is shifted along a curved path.

The invention furthermore relates to the method for producing control data for a laser device which sections a transparent material by focusing optical radiation, wherein the control data predetermine a curved path for a shift of a focus of the optical radiation in the material.

Finally, the invention furthermore relates to a treatment apparatus for creating cuts in a transparent material, wherein the treatment apparatus has a laser device, which is designed to create a cut in a transparent material by focusing optical radiation, and a control device which is connected to the laser device and controls the laser device such that the laser device shifts a focus for the optical radiation in the material along a curved path.

BACKGROUND

Such methods and treatment apparatuses are known in the state of the art. In particular in the field of ophthalmology, such methods and treatment apparatus are used for procedures with which defective vision is corrected. The cuts can be used for example to modify the cornea such that defective vision is remedied. For example, methods are known in which a volume of the cornea is isolated and removed in order to modify the curvature and thus the imaging properties of the cornea to correct defective vision.

The creation of cuts on the eye is likewise necessary in cataract surgery. Within the framework of this surgery, a cloudy crystalline lens is removed. For this removal, it is advantageous to first section the lens in the lens capsule, with the result that it can be removed through a small lateral access opening created surgically.

In these fields of use, as well as in other applications, optical radiation acts inside the material, for example the tissue, which is transparent to the optical radiation. Non-linear processes are usually used which require a focusing of treatment radiation, usually pulsed laser radiation, into the material, i.e. underneath the surface of the material. The creation of a cut then occurs by shifting the position of the focus in the material. According to the understanding this description, the shift of the focus does not necessarily require that radiation is also emitted into the focus at this time. In particular when pulsed laser radiation is used, the focus is continuously moved and laser radiation pulses are only emitted at certain times during the focus movement. Nevertheless the corresponding lens systems or pieces of device for focus movement work continuously, which is why the term "focus shift" here is also understood to mean the corresponding shift of the point at which optical radiation would be focused even if such radiation is momentarily not emitted, e.g. between two laser pulses.

The high focusing of the laser radiation, i.e. a geometrically strongly delimited focus, is of great importance for non-linear effects, as only then can the necessary power densities in the material be achieved. This applies both to non-linear processes in which an individual focus already results in an interaction, and to processes in which several laser radiation pulses which are emitted one after the other interact in order to achieve a material-cutting effect. In this regard, approaches are also known in which laser radiation pulses are emitted at several overlapping focus spots and only the interaction of the several laser radiation pulses in the overlap area leads to material cutting.

The necessary precise focusing of the laser radiation is understandably impaired by the material through which the laser radiation is guided. Since, as already mentioned, the focus lies inside the material when cuts are to be created in the material, cuts can obviously be generated with this principle as a rule only in a direction contrary to the main direction of incidence of the laser radiation, thus from posterior to anterior when used on the eye. Otherwise, parts of the material in which material has already been cut, thus the cut has been already partially constructed, would disrupt the passage of the laser radiation and thus the desired precise focusing. In other words, areas of the cut that are deeper in relation to the direction of incidence of the optical radiation must be cut before areas of the cut that are higher can be created.

A further problem which occurs within the creation of cuts by guiding a focus along a path is the speed of the creation of cuts. The focus is usually deflected by operation of a scanning device. The deceleration, re-positioning or acceleration of the scanning device can substantially prolong the creation of cuts. When used on the eye, not only is this onerous for a patient, as the surgical procedure lasts longer, the expenditure that must be met for precautions against unintended eye movements also increases with the increasing time required for the creation of cuts.

This problem is particularly great when a sectioning of transparent material is to be carried out, thus crossing cuts are required. Because of the crossover points and the fact that the cuts must be constructed in layers contrary to the direction of incidence of the radiation, the deceleration, re-positioning and acceleration of the scanning device leads to a very great prolonging of the creation of cuts.

Although approaches are known in the state of the art for carrying out the deflection movements as continuously as possible, thus for dispensing with deceleration and acceleration processes for the deflection device as far as possible (cf. DE 102008027358 A1), these approaches are however limited to quite particular cut geometries.

When producing cuts in the cornea or the lens, the occurrence of gas bubbles is unavoidable. The more complex the cutting patterns, the greater the risk that the gas bubbles have negative effects and could result in a capsule rupture, for example. The suggested creation of cuts on curved paths of periodically crossing Lissajous figures as suggested in DE 102011085041A1 has shown to be time-efficient. These curves result in a great progress, however still present disadvantages. The surface accessible by Lissajous figures therefore generally consist of a rectangle. But during applications for cuts in the lens, the area of usage is however determined on a circular area as the opening cut is also formed circular due to the overlying capsular sac. A certain proportion of the curved path will thereby be located outside of the area to be processed and must therefore me blended out so that it doesn't result in any material processing. This prolongs the processing period. In the cuts guided from bottom to top on periodic paths, there is however furthermore the risk that gas bubbles result in negative effects due to the focused symmetrical cutting pattern.

SUMMARY OF THE INVENTION

There is still in need, therefore to develop the method or the treatment apparatus of the type named at the outset such that a high sectioning speed can be achieved when creating cross cuts and that this will lead to a better result than in the state of the art.

Example embodiments of the invention include a method for creating cuts in a transparent material by application of optical radiation, whereby the optical radiation is focused on a focus in the material and the focus is moved along a curved path, whereby a harmonic path is used in a view perpendicular to a main direction of incidence of radiation and whereby adjacent curved paths for example don't lie on top of each other in the main direction of incidence of radiation.

Example embodiments of the invention include a method for creating control data for a laser device, which creates cuts in a transparent material by focusing optical radiation, wherein the control data specifies a curved path for a displacement of a focus of the optical radiation in the material, whereby the control data is created so that a harmonic path is used in a view perpendicular to a main direction of incidence of radiation and whereby adjacent curved paths for example don't lie on top of each other in the main direction of the incidence of radiation.

Example embodiments of the invention include a treatment apparatus for creating cuts in a transparent material, wherein the treatment apparatus has a laser device, which is designed to create cuts in a transparent material by focusing optical radiation, and a control device connected to the laser device which is connected to the laser device and controls the laser device such that the laser device shifts a focus on the optical radiation in the material along a curved path, wherein the control device controls the laser device such that a harmonic curve is used perpendicular to a main direction of incidence of radiation and whereby adjacent curved paths preferably don't lie on top of each other in the main direction of the incidence of radiation.

A path is for example also used as the basic figure that forms a planar curve in a view perpendicular to a main direction of incidence of the radiation, which is created through the superimposition of at least one harmonic oscillation each in two orthogonal directions in space.

A general formula for such a basic figure is:

$$\vec{\gamma}(t) = \begin{pmatrix} \gamma_x(t) \\ \gamma_y(t) \end{pmatrix}, [t \in T)$$

whereby $\vec{\gamma}(t)$ is the path, $\gamma_x(t)$ the vibration in direction x, $\gamma_y(t)$ the vibration in direction y, and t is time.

This path has the advantage that a deflection device, which is usually realized as a biaxial scanner, moves according to harmonic oscillations. Usual scanning mirrors achieve their maximum operating speed precisely in this harmonic oscillation mode. The focus can thus be guided along the path at maximum speed. In order to create the desired crossing cuts, a crossing path is used. In one preferred embodiment, the paths in different depths in the material are not positioned exactly one above the other. In order to realize this, the paths for different depths are not periodic to one another. The non-periodicity of the sequential execution of the basic figure is selected so that the basic figure rotates around its symmetrical axis after each execution. The general formula is thereby as follows $$\vec{\gamma}(t; z) = \begin{pmatrix} \cos(\phi(z)) & -\sin(\phi(z)) \\ \sin(\phi(z)) & \cos(\phi(z)) \end{pmatrix} \begin{pmatrix} \gamma_x(t) \\ \gamma_y(t) \end{pmatrix}$$

with $\phi(z) = \dfrac{\phi_1 - \phi_0}{z_1 - z_0} \cdot (z - z_0) + \phi_0$ as the angle of rotation, and $z_o$ as the start value for the z axis.

At the same time as the rotation, the z axis is slowly moved through so that after the basic figure, the next basic figure is both offset in z-direction and rotated by a certain angle. This rotation of cuts ensures that the gas bubbles are not all arranged on top of each other and thus result in a local excess pressure The overall rotation is for example between 20° and 135° from the bottom cut (starting above the posterior capsule) to the top cut (ending underneath the anterior capsule), and especially preferably 45°, 60°, 90° or 120°. This rotation angle ensures a sufficient distribution of the gas bubbles across the surface on the one hand and a removability of the resulting lens fragments on the other. The angle that the basic figure is rotated by after each step is therefore the result from the angle of the overall rotation divided by the number of z steps.

If the selected total rotation angle coincides with the multiplicity of the rotation symmetry of the basic figure at the end of the sequential execution, then all the partial sections accounting for the basic figure scan patches along the z scan, which form a clearly recognizable continuous area in the projection (viewing direction of the surgeon) due to the blistering. The surgeon recognizes both the OP scan progress and the photo disruptive effect in the different layers of tissue. With a number of 4 it thus results in exactly 4 sectors of 90° and with a number of 6, it results in 6 sectors of 60°.

Alternatively, a slow shift of the cutting pattern in x- or y-direction is also possible. This can be done through a slow shifting of the scanners in x-direction or y-direction. Here, the general formula is:

$$\vec{\gamma}(t; z) = \begin{pmatrix} T_x(z) \\ T_y(z) \end{pmatrix} + \begin{pmatrix} \gamma_x(t) \\ \gamma_y(t) \end{pmatrix}$$

with $T_x(z) = \dfrac{T_{x,1} - T_{x,0}}{z_1 - z_0} \cdot (z - z_0) + T_{x,0}$ und $T_y(z) = \dfrac{T_{y,1} - T_{y,0}}{z_1 - z_0} \cdot (z - z_0) + T_{y,0}$ being the shift values.

For example, the scanner movement starts off-axis at the bottom section and moves upwards so that the scanners intersect the axis approximately in the middle of the lens and move further upward in that direction.

Alternatively, a slow stretching or compression relative to the symmetrical axis of the basic figure is also possible. The path is hereby defined through:

$$\vec{\gamma}(t;z) = \begin{pmatrix} S_x(z) & 0 \\ 0 & S_y(z) \end{pmatrix} \begin{pmatrix} \gamma_x(t) \\ \gamma_y(t) \end{pmatrix}$$

with $$S_x(z) = \frac{S_{x,1} - S_{x,0}}{z_1 - z_0} \cdot (z - z_0) + S_{x,0}$$

$$S_y(z) = \frac{S_{y,1} - S_{y,0}}{z_1 - z_0} \cdot (z - z_0) + S_{y,0}$$

as the x and y components of the stretching.

This makes it possible to adapt the radial measurements of the basic figure to the cutting requirements of the current level (z position). Without such an adaptation, parts of the basic figure would need to be blanked or a complete section to the edge in other levels would need to be omitted.

Alternatively, a change of the relative phase of the position of the laser impulses along the basic figure is also possible. Generally speaking, this results in a curved path for:

$$\vec{\gamma}(t;z) = \begin{pmatrix} \gamma_x(t + \tau_x(z)) \\ \gamma_y(t + \tau_y(z)) \end{pmatrix}$$

with $$\tau_x(z) = \frac{\tau_{x,1} - \tau_{x,0}}{z_1 - z_0} \cdot (z - z_0) + \tau_{x,0} \text{ und}$$

$$\tau_y(z) = \frac{\tau_{y,1} - \tau_{y,0}}{z_1 - z_0} \cdot (z - z_0) + \tau_{y,0}$$

as a relative phase change.

The position of the laser impulses between two basic figures can thus be changed so that the spots of the one basic figure usually lie precisely in the gaps of the others. In this way, the geometric proximity of the gas bubbles of adjacent sequential executions of the basic figure is also reduced. It is also within the framework of the invention to transfer the basic figures into each other by simultaneously shifting, rotating, or stretching them by appropriately controlling the scanner in x direction and/or y direction in amplitude and phase position of the frequency components involved.

Example embodiments of the invention include that a rotation of the basic figure around its own axis is performed with a constant z-value so that there is a complete separation at this level (360°/number of the symmetry). For example, this level is located in the center of the lens. As the individual paths are spaced more closely in the center than at the edge of the lens, more spots are set in the center of the lens than at the edge in this process. Lenses, in which the center is harder as usual, can therefore be cut more easily using this approach.

It is also within the scope of the invention to reduce the number of paths to such an extent that a complete separation only takes place in the center and the level is just perforated in the edge region, so to speak. The number of selected paths must therefore only be so big that a simple removability of the lens during the subsequent distance of the lens of the eye is ensured. The number of paths is thereby preferably chosen depending on the hardness of the lens. This way, less paths can be chosen for soft lenses than for hard lenses. This facilitates that the time required for the respective level is short.

Alternatively, laser impulses can also only be set in the inside area of the lens. It is furthermore also possible to use completely separating basic figures at more than one level, and to create several cut surfaces crosswise to the optical axis this way.

In some of the versions according to the invention, traveled paths are situated offset to each other at different depths and these results in the desired lateral cut surfaces which will generally be skewed to the main direction of incidence of the radiation.

The curved paths are expediently created larger than the area in which the cuts are formed in the material. In the areas in which the curved paths extend beyond this area, the optical radiation is for example switched off or deactivated in respect of its material-cutting effect. This can be carried out, for example by a deliberate defocusing, change of spectral parameters, attenuation of the pulse energy, extension of the pulse duration, etc. Rendering laser radiation pulses harmless is already known in the state of the art in another connection.

For this, it is favorable if an area of cut has been or is defined, if the curved paths are created or designed larger than the area of cut and the optical radiation on sections of the trajectory which lie outside of the area of cut is switched off or is modified such that it does not create cuts in the transparent material. In the treatment apparatus, the control device controls the laser system analogously in areas in which the curved paths lie outside of a predetermined area of cut such that the optical radiation is switched off or modified such that it does not create cuts in the transparent material.

After the complete processing of the cuts, it thus results in a generally skewed grid structure, which however does not have any negative influence on the actual purpose of the cuts, namely the sectioning of the lens tissue into removable pieces.

The treatment apparatus for example has a scanning device, which has two scanning mirrors, which deflect about axes that cross each other and a focus-shifting device which moves the focus perpendicularly thereto and along the main direction of incidence, wherein the control device controls the focus-shifting device such that, after one pass through the basic figure, the focus position is shifted contrary to the main direction of incidence by a distance to effect a contiguous material cutting of the successive passes through the shifted, rotated, compressed, or stretched basic figure. The basic figure can thereby be a harmonic or also double-harmonic curve.

The Lissajous figures known from the state of the art (DE102011085047A1) are curves with two frequency components, but only one in of them towards one spatial direction each:

In contrast, the double harmonic curves comprise at least two frequency components, which may exist in both spatial directions. One thus obtains a great multitude of curve shapes whose concrete form depends on the frequency ratio, but especially also on the Fourier coefficients.

Of particular interest are the double harmonic curves, a hypocycloid, or a hypo trochoid in a special case. It is thereby favorable to select suitable parameters for the creation of curves.

Particular advantages of these curves are
  Restriction to an envelope circle (a blanking out is thus not required in contrast to the state of the art)
  Low periodicity
  Many overlaps of the central zone
  Sufficiently quick path speed in the central zone The concrete form of these characteristics is adjustable in broad boundaries. If one allows for the Fourier coefficient to also be in relation to each other different from in the examples, an even greater class of curves is accessible which are also within the scope of the invention.

It is understood that the features mentioned above and those yet to be explained below can be used, not only in the stated combinations, but also in other combinations or singly, without departure from the scope of the present invention. The description of method features for material cutting or for producing control data likewise also relates to a corresponding embodiment of the control device which controls the treatment apparatus. Analogously, features which are described in respect of the treatment apparatus, in particular its control device, are likewise relevant for the corresponding method for treatment of material or producing control data.

The production of control data can be carried out separately from, i.e. independently of the treatment apparatus. Naturally, it presupposes corresponding knowledge about the treatment apparatus, for which the control data are provided.

BRIEF DESCRIPTION OF THE DRAWINGS

The invention is explained in further detail below by way of example with reference to the attached drawings which also disclose features of embodiments of the invention. There are shown in.

DETAILED DESCRIPTION

Figure 1:
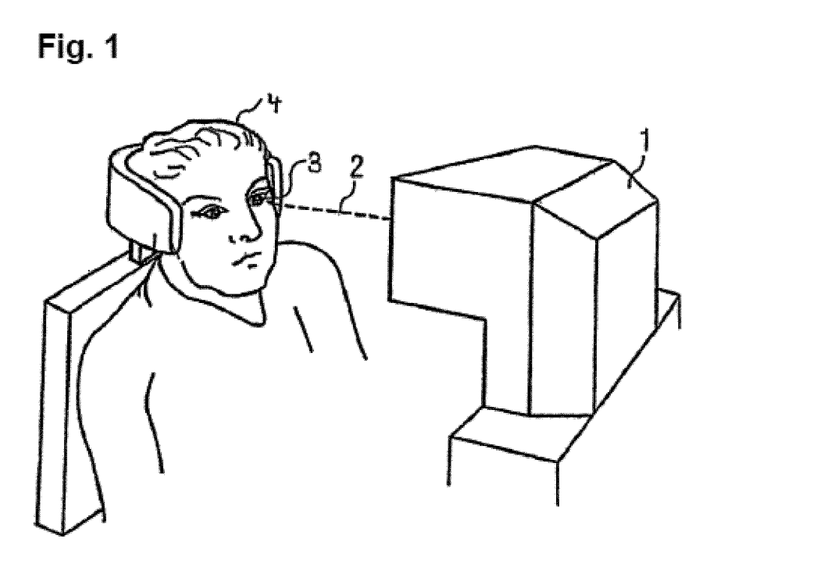
FIG. 1 is a schematic representation of a treatment apparatus for ophthalmology procedures, in particular for correcting defective vision.

FIG. 1 depicts a treatment apparatus 1 for eye surgery. For example an eye-surgery process which is similar to that described in EP 1 159 986 A2 or U.S. Pat. No. 5,549,632 can be carried out with it. The treatment apparatus 1 creates a material cutting in transparent material using treatment laser radiation 2. This material cutting can be e.g. a creation of cuts, in particular the treatment apparatus for correcting defective vision can bring about a change on an eye 3 of a patient 4. The defective vision can include hyperopia, myopia, presbyopia, astigmatism, mixed astigmatism (astigmatism in which there is hyperopia in one direction and myopia in a direction at right angles thereto), aspheric errors and higher-order aberrations. The material cutting can, however, also be used in the field of ophthalmology on other tissues of the eye, e.g. for sectioning the crystalline lens in cataract surgery. Where reference is made to eye surgery below, this is to be understood in each case only by way of example and not as limiting.

In the embodiment example described, the components of the apparatus 1 are controlled by an integrated control unit, which, however, can of course also be formed as a stand-alone unit.

Figure 2:
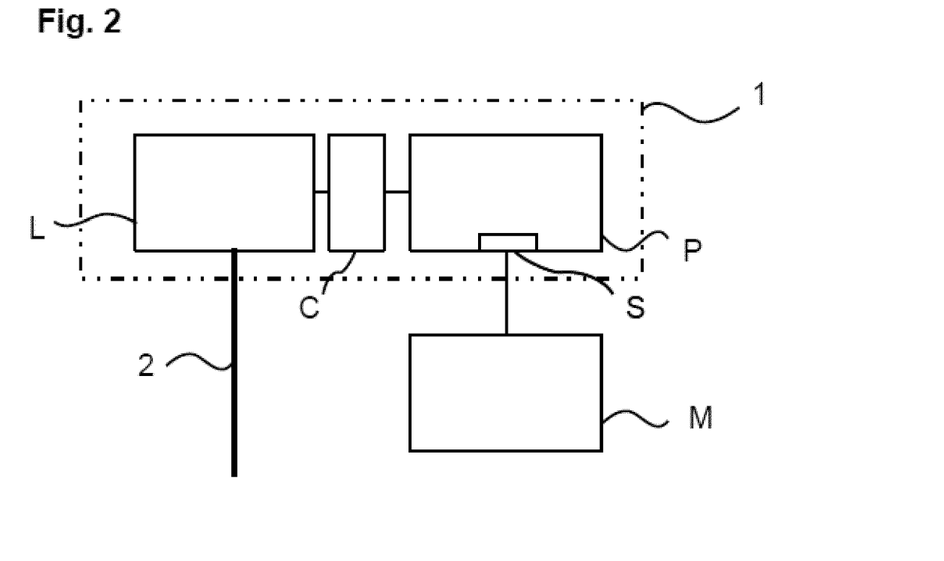
FIG. 2 is a schematic representation with regard to the structure of the treatment apparatus of FIG. 1.

FIG. 2 depicts the treatment apparatus 1 schematically. In this variant it has at least three pieces of devices or modules. Laser device L emits the laser beam 2 onto the material, e.g. the eye 3, and adjusts the position of the focus in the material in three spatial directions x, y, z. The adjustment along the main direction of incidence of the optical radiation (z-axis) is called z-axis adjustment, the x- and y-axis adjustment is preferably carried out perpendicular to the z-axis by scanners.

The operation of the laser device L is fully automatic, controlled by integrated or separate control device C. In response to a corresponding start signal the laser device L starts to deflect the laser beam 2 and thereby creates cuts which are constructed in a manner yet to be described.

The control device C operates according to control data which either have been produced by it or have been supplied to it. In the latter case, which is shown in FIG. 2, the control data necessary for operation are supplied from a planning device P to the control device C beforehand as a control data set via control lines not identified in more detail. The determination or transmission of the control data takes place prior to operation of the laser device L. Naturally, the communication can also be wireless. As an alternative to direct communication, it is also possible to arrange the planning unit P physically separated from the laser device L, and to provide a corresponding data transmission channel.

In ophthalmology, the defective vision of the eye 3 is for example, measured with one or more pieces of measuring device M before the treatment apparatus 1 is used. The measured values are then supplied to the control device or the planning device P and form the basis for the production of the control data. In particular, the position and/or extent of an area to be treated, in particular to be sectioned, can be measured.

The control device or the planning device P produces the control data set from the measurement data which have been determined, e.g. for the eye to be treated. They are supplied to the planning device P via an interface S and, in the embodiment represented, come from measuring device M which has previously taken measurements of the eye of the patient 4. Naturally, the measuring device M can transfer the corresponding measurement data to the planning device P or directly to the control device C in any desired manner.

For example, the control data set is transmitted to the control device and, in another example, operation of the laser device L is blocked until there exists a valid control data set at the laser device L. A valid control data set can be a control data set which in principle is suitable for use with the laser device L of the treatment apparatus 1. Additionally, however, the validity can also be linked to further tests being passed, for example whether details additionally stored in the control data set concerning the treatment apparatus 1, e.g. an apparatus serial number, or concerning the patient, e.g. a patient identification number, correspond to other details that for example have been read out or input separately at the treatment apparatus as soon as the patient is in the correct position for the operation of the laser device L.

The transmission of the measurement data and/or of the control data can be by means of memory chips (e.g. by USB or memory stick), magnetic storage (e.g. disks), or other data storage devices, by radio (e.g. WLAN, UMTS, Bluetooth) or wired connection (e.g. USB, Firewire, RS232, CAN-Bus, Ethernet etc.). A direct radio or wired connection has the advantage that the use of incorrect measurement data is ruled out with the greatest possible certainty. This applies in particular when the patient is transferred from the measuring device M or pieces of measuring device to the laser device L by use of a support device (not represented in the figure) which interacts with the measuring device M and the laser device L respectively such that the respective devices recognize whether the patient 4 is in the respective position for measurement or introduction of the laser radiation 2. The transmission of the measurement and defective-vision data to the treatment apparatus 1 can also take place simultaneously with bringing the patient 4 from the measuring device M to the laser device L.

It is, for example, facilitated that the control device or the planning device P always produces the control data set belonging to the patient 4 and an erroneous use of an incorrect control data set for a patient 4 is as good as ruled out.

In the embodiment described, the laser radiation 2 is emitted as a pulsed laser beam focused into the material, e.g. the eye 3. The pulse duration produced by the laser device L in this case is e.g. in the femto-second range, and the laser radiation 2 acts by non-linear optical effects in the material, e.g. the crystalline lens or cornea. The laser beam has e.g. 50 to 800 fs short laser pulses (preferably 100-400 fs) with a pulse repetition frequency of between 10 kHz and 10 MHz The type of material-cutting effect which the treatment apparatus 1 uses with the laser radiation, however, is of no further relevance for the following description, in particular there is no need to use pulsed laser radiation. The only important thing is that a focus of machining radiation 2 in the material is shifted along a path.

The treatment apparatus 1 forms a cut in the material, the shape of which cut depends on the pattern with which the laser-pulse foci are/become arranged in the tissue. The pattern in turn depends on the path along which the focus is shifted. The path predetermines target points for the focus position at which one or more laser pulse(s) is (are) emitted and ultimately defines the shape and position of the cut.

Figure 3:
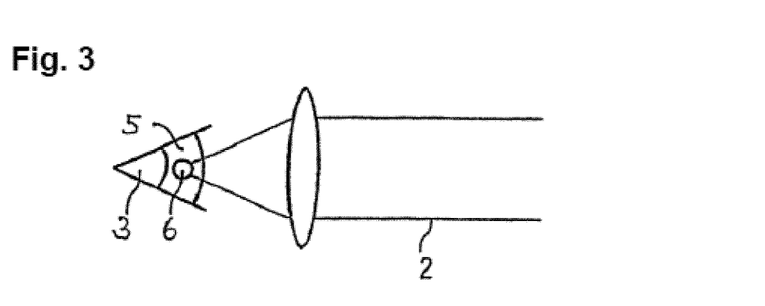
FIG. 3 depicts a basic principle for introducing pulsed laser radiation into the eye with the treatment apparatus of FIG. 1.

A possible mode of operation of the laser beam 2 is indicated schematically in FIG. 3. It is focused into the material, e.g. the cornea 5 or lens of the eye, by means of a lens system of the laser device L not identified in more detail. As a result there forms in the material a focus 6 in which the energy density of the laser radiation is so high that, in combination with the pulse length, a non-linear effect occurs. For example, each pulse of the pulsed laser radiation 2 can create at the respective site of the focus 6 an optical breakthrough in the material, e.g. in the cornea 5 or lens, which is indicated schematically in FIG. 3 by way of example by a plasma bubble. As a result, material, e.g. tissue, is cut owing to this laser pulse. When a plasma bubble forms, the tissue layer cutting comprises a larger zone than the spot covered by the focus 6 of the laser radiation 2, although the conditions for creating the breakthrough are achieved only in the focus. In order for an optical breakthrough to be created by every laser pulse, the energy density, i.e. the fluency, of the laser radiation must be above a certain threshold value which is dependent on pulse length. This relationship is known to a person skilled in the art from, for example, DE 695 00 997 T2.

Alternatively, a material-cutting effect can also be produced by the pulsed laser radiation by emitting several laser radiation pulses in one area, wherein the spots 6 overlap for several laser radiation pulses. Several laser radiation pulses then interact to achieve a tissue-cutting effect. For example the treatment apparatus 1 can use the principle which is described in WO 2004/032810 A2.

The treatment apparatus 1 creates in the cornea 5 or in the lens of the eye 1 a sectioning of the tissue by forming cuts as a grid (naturally, this is not limited to ophthalmology). By this grid represented schematically in FIG. 4, transparent material 1a is to be sectioned, with the result that it can be removed.

Figure 4:
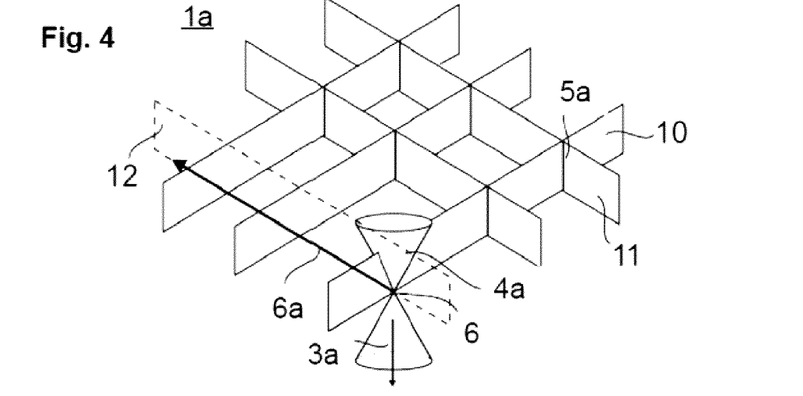
FIG. 4 is a schematic representation to illustrate a first grid of cuts which is to be created with the treatment apparatus of FIG. 1.

In the transparent material 1a, a grid of cuts 10, 11, 12 is created by shifting the focus 6 of the laser radiation 2, which propagates along a direction of propagation 3a, inside the transparent material 1a along a path 6a. The path 6a is chosen such that it follows the cuts 10, 11 and 12 and travels along these.

When controlling the laser device L, the control device C makes sure that the cuts 10, 11 and 12 are constructed by the trajectory 6a only contrary to the main direction of propagation 3a of the laser beam 2. Otherwise, the focus 6 would be disrupted by material cuts that are already present (for example cuts) in the incident light cone 4a. This problem is in principle posed in the case of material cutting by focused optical radiation and is particularly great at crossover points 5a of the cuts 10, 11 and 12 in the use described by way of example.

The cut 12 represented by a dashed line illustrates that the path 6a is arranged in different height levels in order to avoid the mentioned laser focus disruption in the incident light cone 4a. The path 6a is therefore formed such that it works through all cuts 10, 11 and 12 in the lowest height level first, i.e. in the height level that is the furthest removed from the laser device L in relation to the main direction of incidence 3a. If, with the path 6a, the cut lines of all cuts 10, 11 and 12 were worked through with it in this height level, the same is carried out for the next height level which lies closer to the laser device L in relation to the main direction of incidence 3a.

Figure 12:
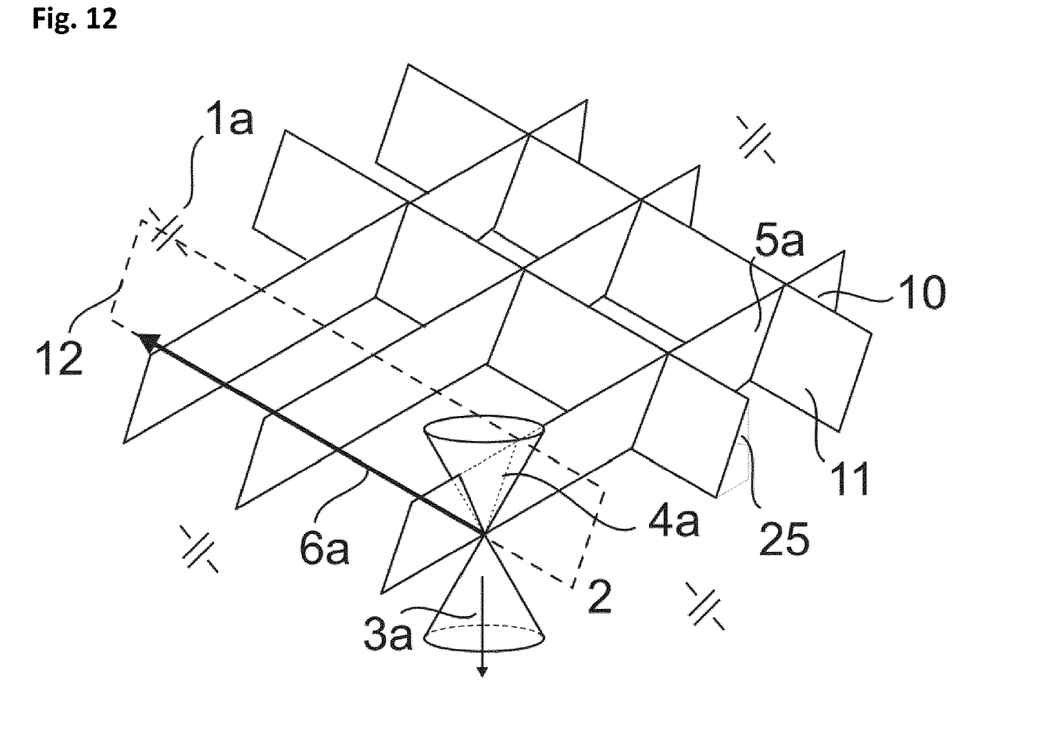
FIG. 12 is a schematic representation to clarify a second grid from cut surfaces that is supposed to be created with the treatment apparatus of FIG. 1.

To provide a better overview, the individual paths 24 are used to create the cut surfaces 10, 11, 12 from FIG. 12 are depicted by way of example once more.

Figure 5:
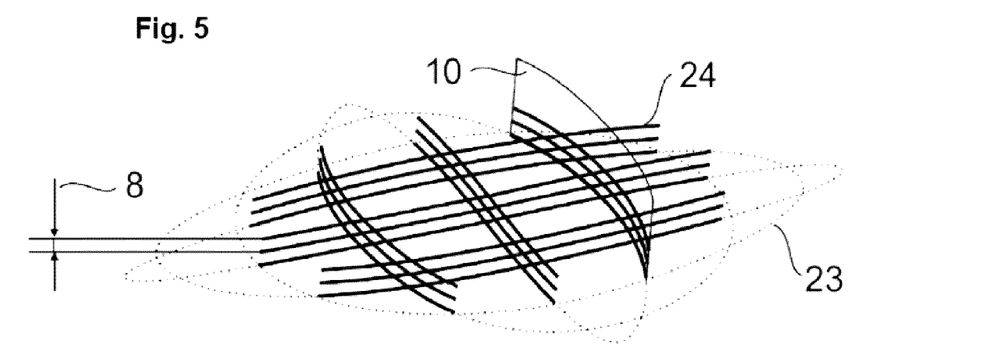
FIG. 5 is a schematic representation to illustrate the creation of the schematically represented cut of FIG. 4.

In order to avoid a time-consuming deceleration and re-positioning or acceleration of the focus deflection, the grid of cuts represented schematically in FIG. 4 is generated by movement of the biaxial deflection of the laser device L on a path 23 in the shape of a planar path, which is represented in FIG. 5. The basic figure only has to be provided in respect of the x-/y-deflection, thus as seen along the main direction of incidence 3a. Only from this view must a closed, thus periodic, path 6a be provided.

There are thus two variants: Firstly, the path 6a can lie in one height plane. Then the z-position of the focus 6 remains constant as long as the basic figure is traveled, and the path 6a is also closed in three-dimensional space. The control data or the control by the control device thus effect in each height level a closed path 23 on which the focus is guided. This is called variant 1 below. Secondly, the z-adjustment can adjust the position of the focus, while the basic figure is being traveled. This is called variant 2 below. Unless differences in these two variants are explicitly discussed, the statements made here apply to both variants.

The basic figure is preferably formed by a superimposition of harmonic oscillations, x-/y-deflection devices can thus be moved continuously with harmonic sine or cosine movements. A high working speed is the result.

In sections 23 of the path 6a which run outside of the zone in which the intended cuts are to be created (the cut surface 10 is also drawn in by way of example in FIG. 5), the laser beam is blanked, i.e. switched off or deactivated in respect of its treatment effect. The laser radiation is active and cuts tissue only in sections 24 of the path 6a which run inside the zone in which cuts are to lie. FIG. 5 shows, dotted, the sections 23 of the path 6a, in which the laser beam is blanked. The sections 24 of the path 6a in which the radiation brings about a material cutting are drawn in with continuous lines.

FIG. 5 shows furthermore the spacing 8 between the height levels, in which in each case the basic figure is traveled. In contrast to the state of the art, the desired sectioning of the transparent material 1a can also be achieved, when the basic figure is stretched or compressed a bit, its origin is slightly shifted or it is rotated as is shown by way of example on the angle 25.

When creating the cut surfaces 10, 11, and 12, in accordance with variant 1, the curved path 6a may comprise a complete run at each vertical level (or several runs as mentioned in the general part of the description) through the basic figure.

To create the cut surfaces it is however also possible, according to variant 2, to execute the deflection along the main direction of incidence 3a during the basic figure. The control device or the control data created by the planning unit effect a z-adjustment of the focus 6 either in a short path section that then represents a transition between two vertical levels of variant 1, or a continuous z-adjustment of the focus 6. With reference to the equations mentioned above, during which the scan path repeats with a basic frequency $f_0$, during continuous z-adjustment of the focus 6, the z-coordinate of the focus 6 moves in the duration $1/f_0$ by the desired distance 8 that superimposed curved path sections should have.

Figure 6:
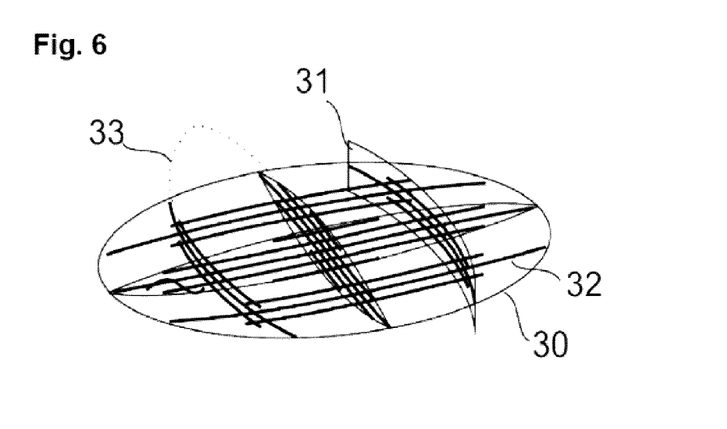
FIG. 6 is a representation similar to FIG. 5, but with a delimitation of cuts to a machining zone

FIG. 6 shows, by way of example, a sectioning of a crystalline lens 30, which is carried out for cataract surgery or also of a different lens-shaped area (i.e. also in the cornea of the eye). The treatment apparatus 1 creates cuts 31, by travelling the curved path 6a. In sections 32 of the path which lie inside the lens 30, the laser radiation 2 is active. In sections 32 of the curved path which lie outside of the crystalline lens 30, the laser radiation 2 is blanked. Naturally, this principle can also be applied to other materials and illustrates that the combination of activating the laser radiation inside a desired volume and blanking outside of the desired volume makes possible a rapid construction of crossing cuts.

Particularly preferred curved paths or basic figures are clarified in the following.

Figure 7:
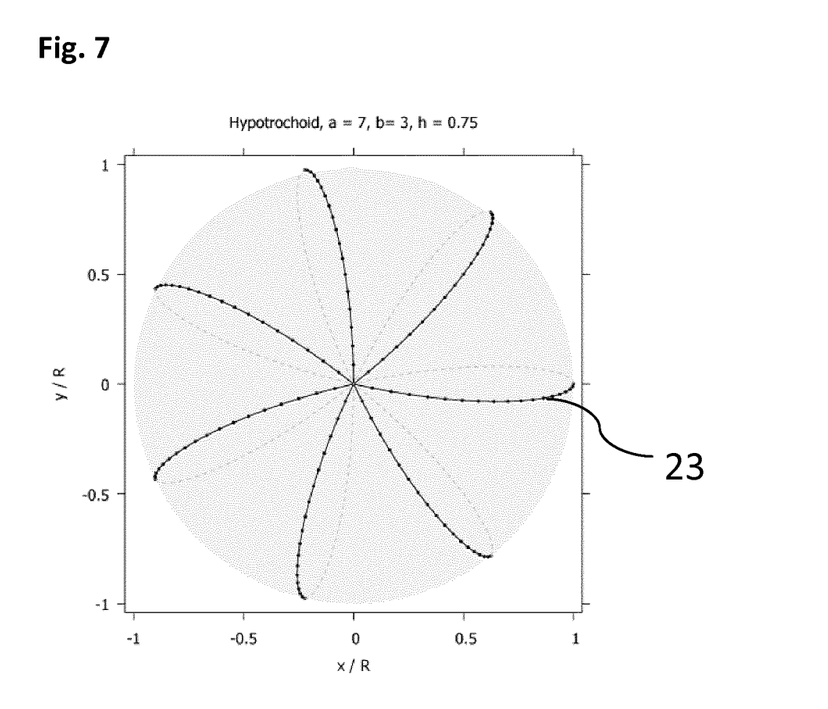
FIG. 7 depicts a hypotrochoid as a sample curve

FIG. 7 shows a hypotrochoid with the parameters $$a = 7, b = 3, \frac{1}{k} = k = \frac{a-b}{b}$$

The general formula for this curve is provided by $$x(t) = \frac{R}{2} \cdot \left[\cos(\omega t) + \cos\left(\frac{\omega t}{k}\right)\right]$$

$$y(t) = \frac{R}{2} \cdot \left[\sin(\omega t) - \sin\left(\frac{\omega t}{k}\right)\right]$$

$$z(t) = \frac{R}{2}(e^{+i\omega t} + e^{-\frac{i\omega t}{k}})$$

R is thereby the radius of the circle describing the surface to be processed and $\omega$ is the maximum angular velocity of the scanners used.

The periodicity T therefore results from $$T = (a-b)\frac{2\pi}{\omega} = 4 \cdot \frac{2\pi}{\omega}$$

and the effective processing time (laser-on time) from $$T_{on} = \frac{T}{2} = 2 \cdot \frac{2\pi}{\omega}$$

The total length of the curve to be traveled is $$L = 24.407 \cdot R$$

Whereby the effective length is $$l = \frac{L}{2} = 7.204 \cdot R.$$

Figure 8:
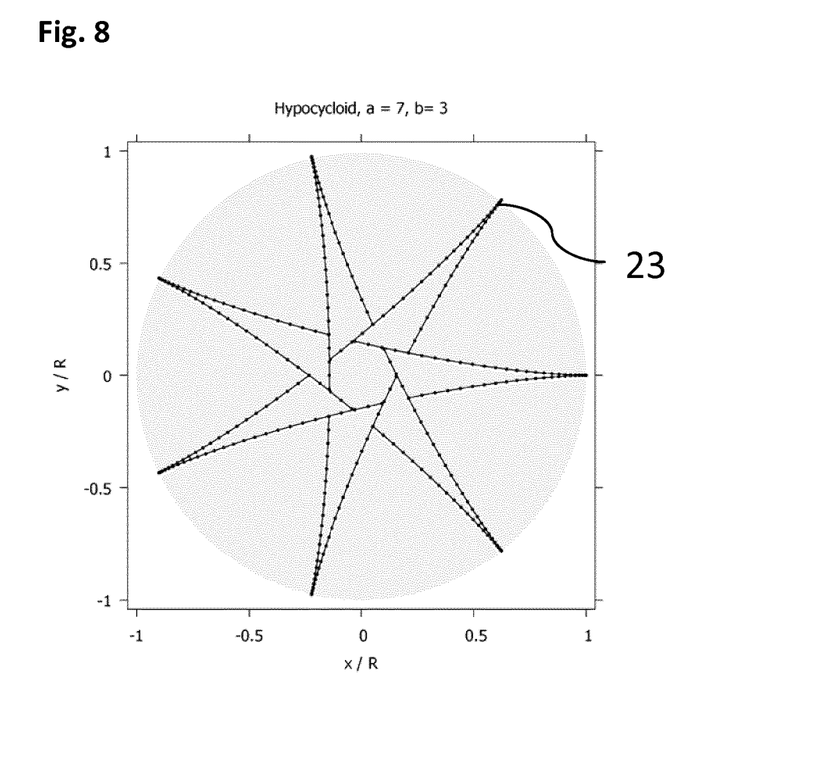
FIG. 8 depicts a hypocycloid as a sample curve

FIG. 8 shows a hypocycloid with the parameters $$a = 7, b = 3, k = \frac{a-b}{b}$$

The general formula for this curve is provided by $$x(t) = \frac{R}{1+k} \cdot \left[\cos(\omega t) + k \cdot \cos\left(\frac{\omega t}{k}\right)\right]$$

$$y(t) = \frac{R}{1+k} \cdot \left[\sin(\omega t) - k \cdot \sin\left(\frac{\omega t}{k}\right)\right]$$

$$z(t) = \frac{R}{k+1}(e^{+i\omega t} + k \cdot e^{-\frac{i\omega t}{k}})$$

The periodicity T thus results from $$T = (a-b)\frac{2\pi}{\omega} = 4 \cdot \frac{2\pi}{\omega}$$

and the effective processing time (laser-on time) from $$T_{on} = (1 - 0.037) \cdot T = 3.852 \cdot \frac{2\pi}{\omega}$$

The total length of the curve to be traveled is $$L = \frac{96}{7} R = 13.714 \cdot R$$

whereby the effective length is $l = 0.942 \cdot L = 12.922 \cdot R$

The double harmonic curves presented in 7 and 8 are examples from the favorably selected parameters from the classes of the hypotrochoids or hypocycloids, so that a small periodicity, many overlaps of the central zone and a sufficiently constant path velocity are reached in the central zone. In both cases, the frequencies act like 4:3. The amplitude ratios are 1:1 (Hypotrochoids) or 4:3 (Hypocycloids). If one sets the cut-off frequency of the angular scanners to 250 Hz by way of example, there will be a fast movement component at 250 Hz and a slow one at 187.5 Hz. The time required for a complete rotation is 16 ms. If one additionally adds the radius of the enveloping of 3.5 mm, it results in a path velocity of about 3 m/s. In case of a repetition rate of the laser of, for instance 2 MHz, one achieves pulse intervals of a typical 1.5 μm in the material to be cut. If superimposed cuts are supposed to have the same distance, the overall time for 2,000 layers (3 mm axial length) is 32 seconds. As can be seen easily, these basic figures are especially suited for the sectioning by use of cut surfaces in parallel to the direction of incidence of the optical radiation.

Figure 9:
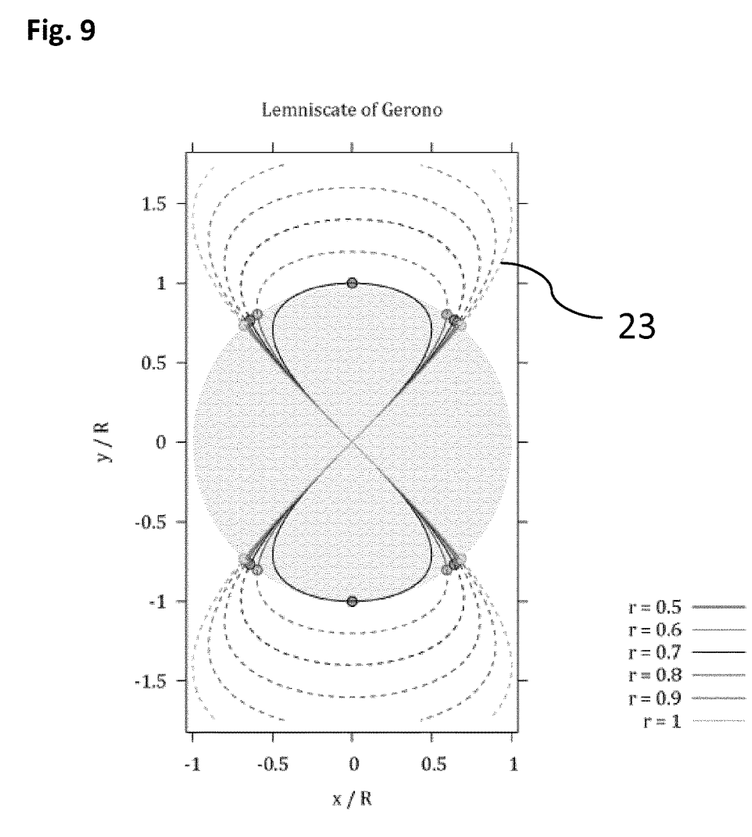
FIG. 9 depicts different curves from Gerono as a sample curve

FIG. 9 shows a group of so-called curves (or lemniscates) of Gerono.

The general formula for this curve is given by $$x(t) = r \cdot R \cdot \sin(\omega t)$$
$$y(t) = 2r \cdot R \cdot \sin\left(\frac{\omega t}{2}\right)$$
$$z(t) = \frac{R}{2}\left[i(e^{-i\omega t} - e^{+i\omega t}) + 2r\left(e^{+\frac{i\omega t}{2}} - e^{-\frac{i\omega t}{2}}\right)\right]$$

With r=0.7 it thus results in a curve of the area to be processed limited precisely by the radius R, the optical radiation therefore doesn't affect any areas located outside of the treatment zone.

The periodicity T results from $$T = 2 \cdot \frac{2\pi}{\omega}$$

and the effective processing time (laser-on time) from $$T_{on} = 0.369 \cdot T = 0.738 \cdot \frac{2\pi}{\omega}$$

Figure 10:
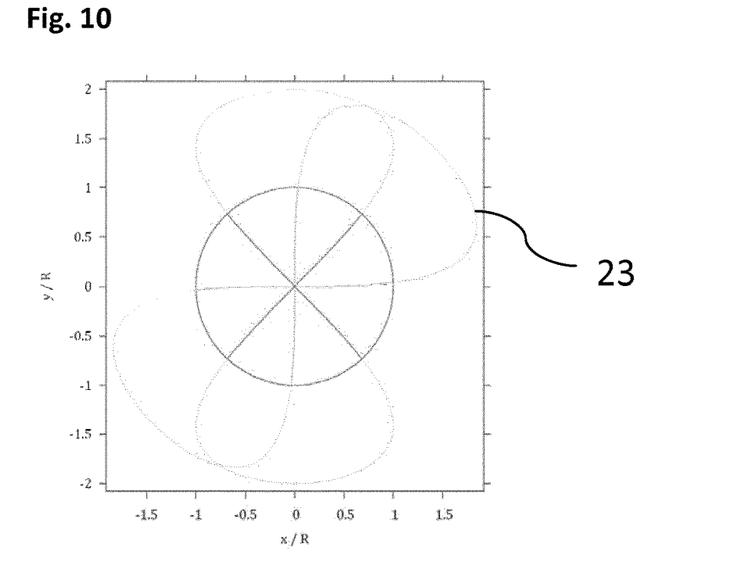
FIG. 10 depicts the application of a curve from Gerono for segmentation

The total length of the curve to be traveled is $L = 8.536 \cdot R$ whereby the effective length is $l = 0.471 \cdot L = 4.017 \cdot R$ By travelling this basic figure under a different angle as shown in FIG. 10, a sectioning can be realized by use of cut surfaces parallel to the direction of incidence of the optical radiation just like in the examples of FIGS. 7 and 8. The basic figure was thereby traveled twice at an angle of 45°, which results in 8 sections.

But it is equally possible to realize a cut vertically to the direction of incidence of the optical radiation by a travelling the basic figure against each other multiple times. The basic figure was traveled 32 times with a respective rotation of 90°/32=28,125° in FIG. 11 by way of example, thus resulting in a very smooth cut.

An alternative embodiment of the invention is described in the following.

The treatment apparatus 1 creates in the cornea 1 or in the lens of the eye 1 a sectioning of the tissue by forming cuts as a grid (naturally, this is not limited to ophthalmology). By this grid represented schematically in FIG. 12, transparent material 1a is to be sectioned, with the result that it can be removed.

In the transparent material 1a, a grid of cuts 10, 11, 12 is created by shifting the focus 6 of the laser radiation 2, which propagates along a direction of propagation 3a, inside the transparent material 1a along a path 6a. The path 6a is chosen such that it follows the cuts 10, 11 and 12 and travels along these.

When controlling the laser device L, the control device C makes sure that the cuts 10, 11 and 12 are constructed by the trajectory 6a only contrary to the main direction of propagation 3a of the laser beam 2. Otherwise, the focus 6 would be disrupted by material cuts that are already present (for example cuts) in the incident light cone 4a. This problem is in principle posed in the case of material cutting by focused optical radiation and is particularly great at crossover points 5a of the cuts 10, 11 and 12 in the use described by way of example.

The cut 12 represented by a dashed line illustrates that the path 6a has to be arranged in different height levels in order to avoid the mentioned laser focus disruption in the incident light cone 4a. The path 6a is therefore formed such that it works through all cuts 10, 11 and 12 in the lowest height level first, i.e. in the height level that is the furthest removed from the laser device L in relation to the main direction of incidence 3a. If, with the path 6a, the cut lines of all cuts 10, 11 and 12 were worked through with it in this height level, the same is carried out for the next height level which lies closer to the laser device L in relation to the main direction of incidence 3a. But the basic figure of the path 6a is now modified such that it is not superimposed with the path just traveled in the main direction of incidence 3a.

Figure 13:
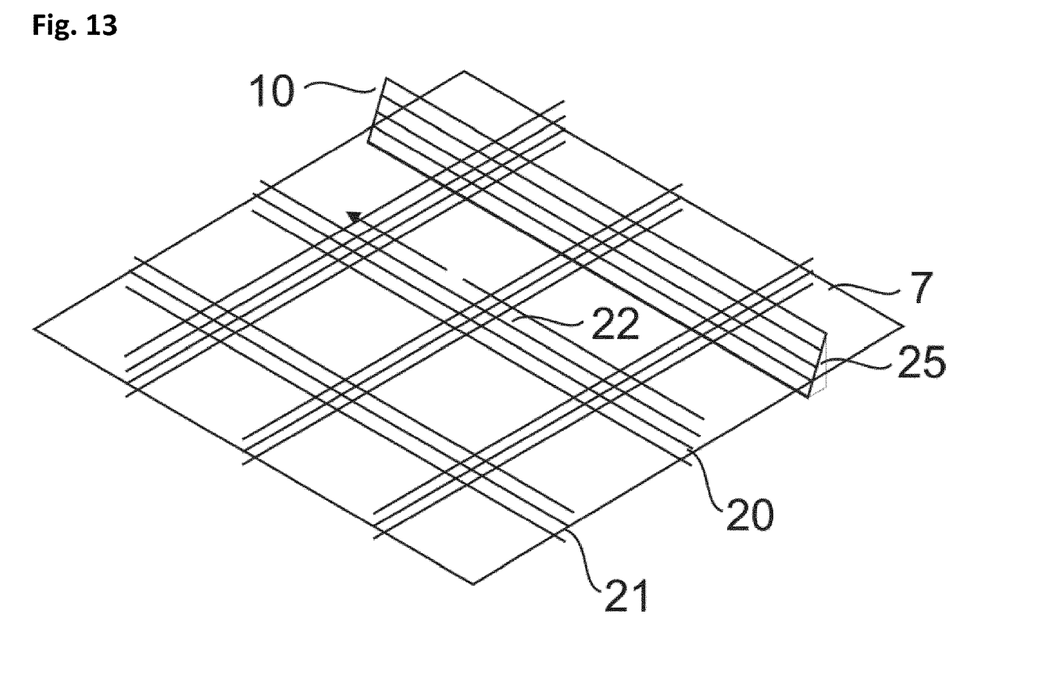
FIG. 13 is a schematic representation to clarify the creation of the schematically shown cut surface of FIG. 12.

To provide a better overview, the individual paths 20, 21, 22, which are used to create the cut surfaces 10, 11, 12 from FIG. 12 are illustrated in FIG. 13 once again by way of example. As can be clearly seen, the paths 20, 21, 22 are not superimposed, but are offset to each other by an angle 25 as the travel of the basic figure from the z-level illustrated by way of example to the next z-level was modified as described above.

Figure 14:
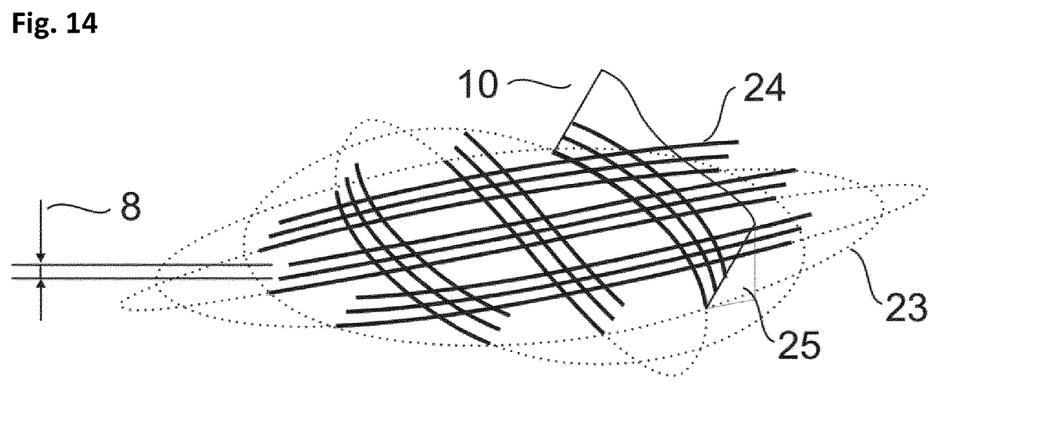
FIG. 14 is a representation similar to FIG. 13, but with a limitation of cut surfaces on a treatment area.

In order to avoid a time-consuming deceleration and re-positioning or acceleration of the focus deflection, the grid of cuts represented schematically in FIG. 12 is generated by movement of the biaxial deflection of the laser device L on a planar path 23, which is represented in FIG. 14. The basic figure only has to be provided in respect of the x-/y-deflection, thus as seen along the main direction of incidence 3a. Only from this view must a closed, thus periodic, path 6a be provided.

There are thus two variants: Firstly, the path 6a can lie in one height plane. Then the z-position of the focus 6 remains constant as long as the basic figure is traveled, and the path 6a is also closed in three-dimensional space. The control data or the control by the control device thus effect in each height level a closed path 23 on which the focus is guided. This is called variant 1 below. Secondly, the z-adjustment can adjust the position of the focus, while the basic figure is being traveled. This is called variant 2 below. Unless differences in these two variants are explicitly discussed, the statements made here apply to both variants.

The basic figure is preferably formed by superimposition of harmonic scintillations, x-/y-deflection devices with harmonic sine or cosine movements can thus be moved continuously. A high working speed is the result.

In sections 23 of the path 6a which run outside of the zone in which the intended cuts are to be created (the cut 10 is also drawn in by way of example in FIG. 5), the laser beam is blanked, i.e. switched off or deactivated in respect of its treatment effect. The laser radiation is active and cuts tissue only in sections 24 of the path 6a which run inside the zone in which cuts are to lie. FIG. 5 shows, dotted, the sections 23 of the path 6a, in which the laser beam is blanked. The sections 24 of the path 6a in which the radiation brings about a material cutting are drawn in with continuous lines.

FIG. 14 furthermore shows the spacing 8 between the height levels in which in each case the basic figure is traveled. Contrary to the state of the art, the desired sectioning of the transparent material 1a is also achieved, if the basic figure is stretched or compressed a bit in each height level, if its origin is slightly shifted, or if it is rotated as is represented at angle 25 by way of example.

To create the cuts 10, 11 and 12, according to variant 1 the path 6a can comprise, in each height level, one full pass (or, as mentioned in the general part of the description, several passes) through the basic figure.

To create the cuts, according to variant 2 it is, however, likewise possible to carry out the shift along the main direction of incidence 3a during the basic figure. The control device or the control data produced by the planning device effecting a z-adjustment of the focus 6 either in a short path section, which then represents a transition between two height levels of variant 1, or effecting a continuous z-adjustment of the focus 6. In relation to the above-mentioned equations, in which the scanning path is repeated with a base frequency $f_0$, the z-coordinate of the focus 6 moves, in the case of continuous z-adjustment of the focus 6, in the time period $1/f_0$, by the desired distance 8 which path sections lying one above the other are to have.

Figure 15:
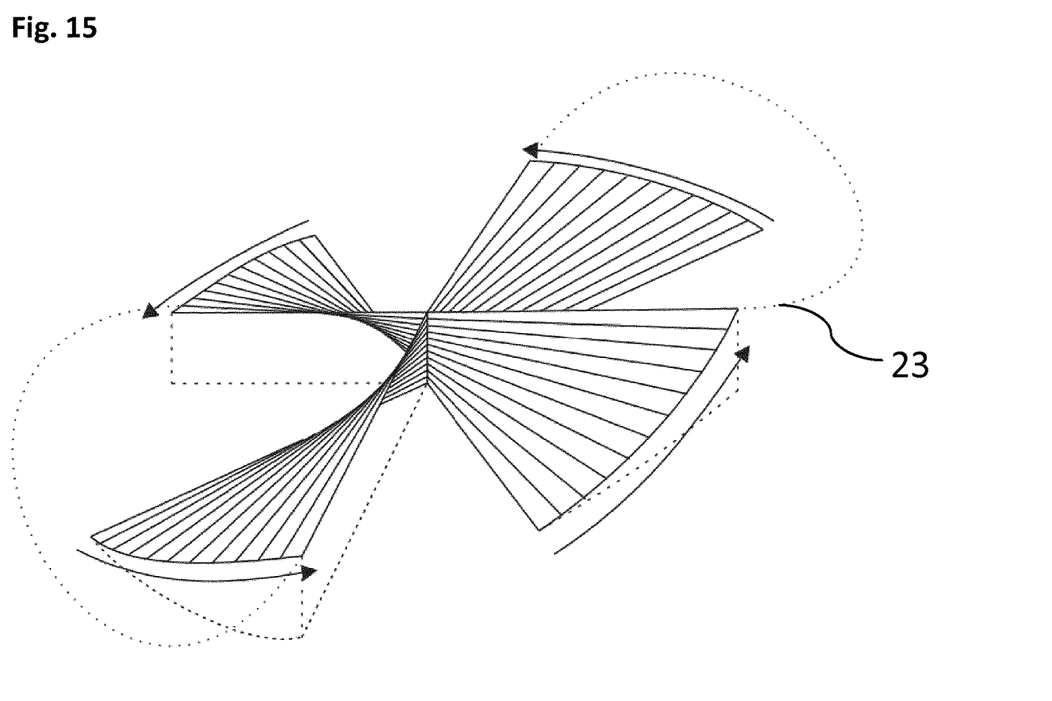
FIG. 15 depicts a further representation to clarify the creation of the schematically shown cut surface of FIG. 12 for a larger z area.

FIG. 15 shows once again by way of example the ratios with a 4-digit basic figure that is rotated by a low angle after each travel. When this angle is determined such that just a quarter circle (due to the basic figure that is tetramerous) was filled with paths 24, it is easy to see that the treating physician can thereby follow the progress of the division of the crystalline lens in a simple manner. If the entire surface was filled with paths, the treatment has been completed and the intended section of the crystalline eye lens has been divided into removable parts. The following features can additionally be realized:

The laser radiation can also be blanked on particular sections of the path inside an area in which cuts lie if the course of the path on the basic figure in those areas does not correspond to a desired cutting pattern.

The height levels need not be planes in the mathematical sense. In particular in the case of a curvature of the image field and/or when curved material is machined, the height levels can be curved 2D manifolds.

In the control of scanners, the amplitude attenuation and phase retardation of the x-/y-deflection device can be determined and taken into account by providing corresponding counterbalancing offsets of the amplitude and phase of the deflection control at high frequencies.

The frequencies of the deflection on the basic figures can take into account the maximum spacing of spots which successive laser pulses are to strike.

Naturally, the cutting pattern created with the basic figure can be supplemented by further cut elements, for example a cylinder jacket as outer delimitation of the treated volume area. In order additionally to also divide the parts of the transparent material 1a created by the cuts 10, 11 and 12 perpendicular to the direction of propagation 3a, cuts which extend substantially perpendicular to the main direction of incidence 3a can also be created between individual height levels.

The cuts created using the basic figure can be used to section eye tissue, for example the crystalline lens or the cornea. It is also possible to effect by the crossed cuts a targeted weakening of a material. In the field of eye surgery, this can be e.g. an intrastromal weakening of the cornea in order to influence the balance between intraocular pressure and cornea strength such that a desired change in the shape of the front surface of the cornea is achieved.

The harmonic movement may also be superimposed by other movements. A parts scanning system that has a large scan area and whose scanning course is freely programmable, however therefore has a comparatively slower scanning speed may be enabled to a quickest possible execution of the scanning figure by programming it with a harmonic scanning path. In the meantime, a fast scanner that has however only a smaller scan area or is also limited in the selection of the scanning curve (e.g. resonant scanner), may superimpose a small fast scanning motion and may therefore execute a scanning area in the form of a band along the harmonic figure.

Figure 16:
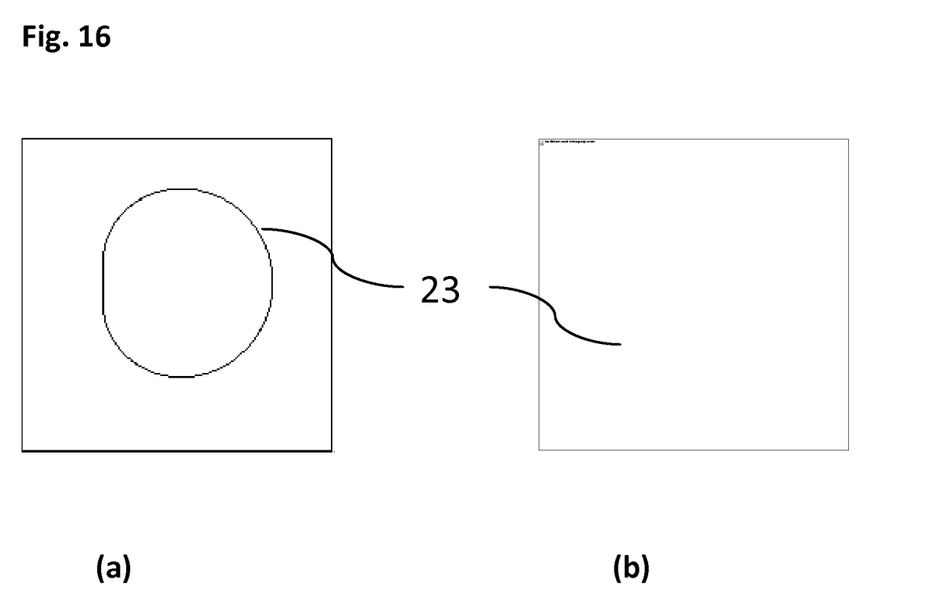
FIG. 16 is a schematic representation of more cut surface designs

This way, cut shapes deviating from the cylinder shape may be generated. The basic figures per the invention are thus also suited for the capsulotomy with cut shapes deviating from the cylinder shape. A respective cut shape is represented in FIG. 16 and can be described with the function $$x+iy=e^{i\omega}+0{,}26e^{2i\omega}$$

Instead of a circular opening, an opening can thus be created that deviates from the circular form and possesses a preferred axial direction. A preferred embodiment of the opening is shown in FIG. 16b. This basic figure type can be described with the function $$x+iy=e^{i\omega}+0{,}12e^{3i\omega}$$

for example. The harmonic movement in the x/y level is thereby superimposed through a quick up-down motion in z-direction, which can be executed by a resonant scanner, for example and does not need to be synchronized with the harmonic movement.

Conversely, a quick scanning system may also perform a harmonic movement and may be superimposed on a slow "feed motion". For instance, tunnel-shaped areas may be scanned this way, whereas the quick harmonic motion determines the tunnel cross-section and specifies the slow "feed motion", the direction of the tunnel.

Toric IOL can preferably be implanted with such an opening, especially when its outer shape is adapted to the shape of the opening.

With the basic figures per the invention, it is possible to cut the capsulotomy required for implanting the IOL precisely with a high quality and a high speed.

Lamé curves are also usable as opening geometry for a capsulotomy. Lame curves can be described with the function:

$$\left|\frac{x}{a}\right|^n + \left|\frac{y}{b}\right|^n = 1.$$

Figure 17:
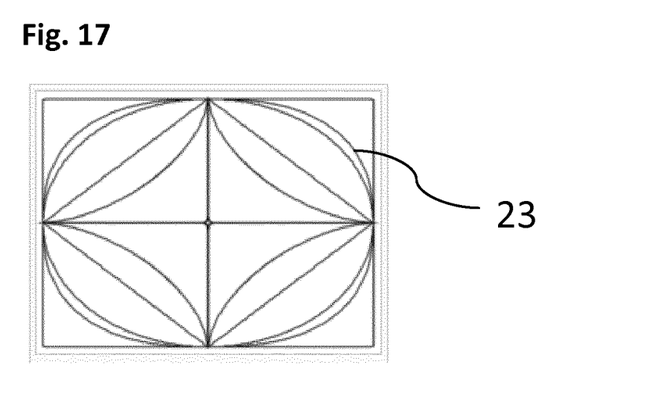
FIG. 17 is a schematic representation of another cut surface design

A and b are thereby the half-axes, whereby 1.05 a<b<1.3 a preferably applies. What is preferred is n greater or equal 2 so that the result is a super ellipse as the geometric shape. It has proved to be especially advantageous if n lies in the range of 2 to 8 and all the more in the range of 3 to 5. Opening geometries of this type are represented in FIG. 17.

The basic figures per the invention are furthermore suited to quickly and effectively perform cuts in the vitreous body. Vitreous strands that exert a pull on the retina can thus be separated. Level cuts according to Gerono that are created according to FIG. 1 are particularly suited for the separation. The planar cutting pattern is thereby selected so that the diameter of the cutting figure is adapted to the diameter of the vitreous strand in the planned cutting level.

Figure 11:
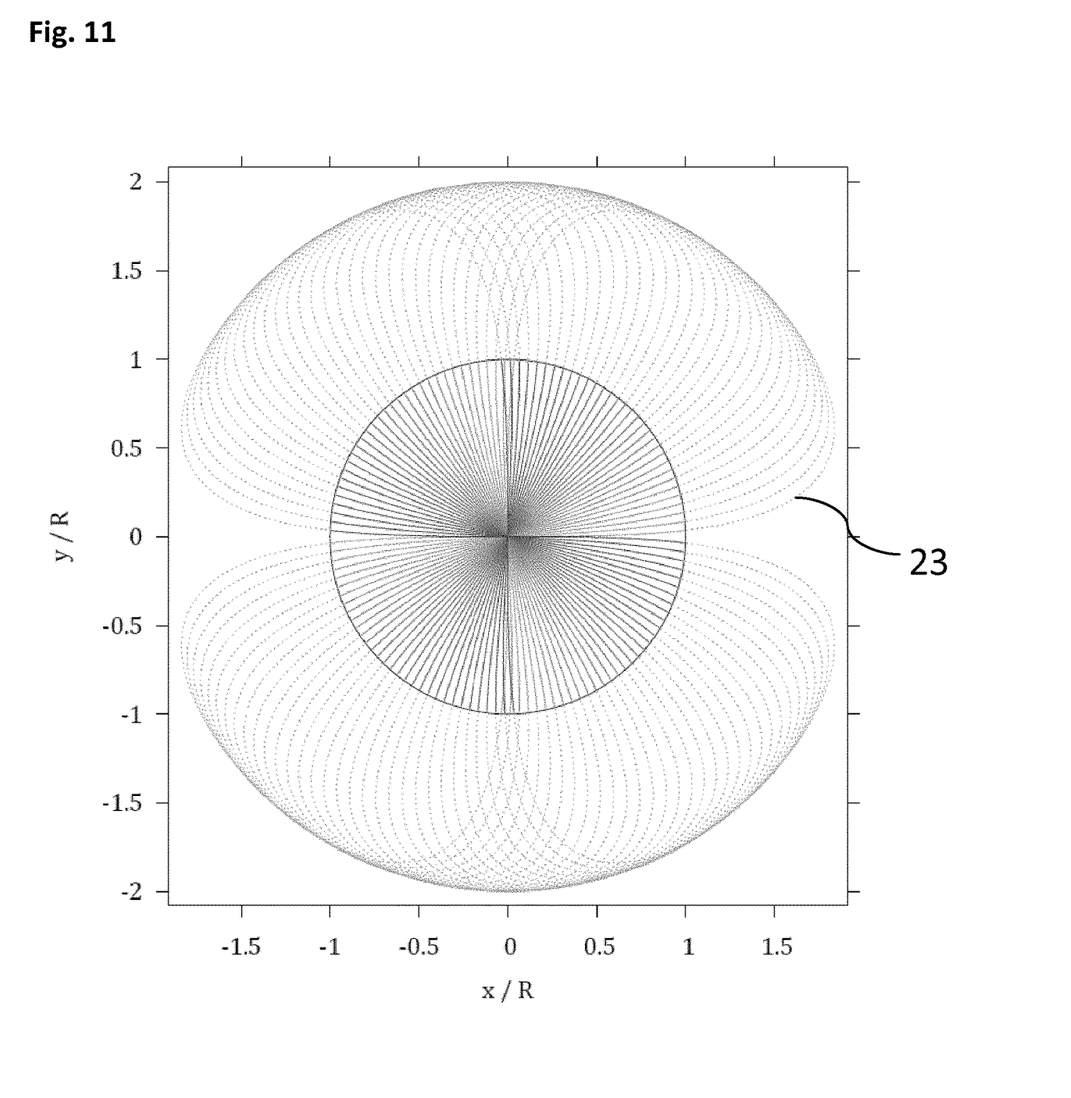
FIG. 11 depicts the application of a curve from Gerono for a planar cut

It is also within the framework of the invention to create cuts for the protection of the retina. The level cuts according to Gerono according to FIG. 11 are also suited for it. A section plane may thus be generated before the retina that is characterized, at least in part, by a higher absorption for the radiation of the laser. This plane forms a protective shield for the retina for the work of the laser in the area between the cornea and this plane.

The cutting pattern according to FIG. 11 is especially well suited, in particular, since the density of the set spot is higher in the middle area and as the area of the fovea is especially protected.

In one embodiment, cutting patterns are generated by superimposition of a slow and a fast movement each. By means of the slow scanning movement, the focus can, with 3 scanners for the x-, y-, and z-direction, for example, be positioned on each point of the eye to be worked on. The cutting patterns themselves are then formed through fast harmonic movements in the three coordinate directions by means of three more scanners for the x-, y-, and z-direction. The amplitude of the fast movement is thereby preferably in the range of 1 to 3 mm.

It is also within the framework of the invention to execute slow and fast scanning movements simultaneously. Cutting patterns may thus be generated in a preferred manner, in which traveled paths are arranged offset to one another in different depth positions, as is represented in FIG. 14 by way of example.

The invention claimed is:

1. A method for creating cuts in a transparent material in eye surgery using femtosecond optical radiation of a femtosecond laser device, comprising:
   focusing the femtosecond optical radiation of the femtosecond laser device at a focus in the material;
   shifting the focus along a curved linear path, the path comprising a series of sequential locations at which femtosecond laser pulses are applied thereby creating the cuts along the path;
   using a simple or double harmonic curve to define the path; and
   wherein adjacent portions of the path at different depths in the transparent material are not superimposed one above another in a main direction of incidence of radiation.

2. The method according to claim 1, further comprising additionally shifting the focus along the main direction of incidence of the radiation and relative to the main direction of incidence.

3. The method according to claim 1, further comprising rotating adjacent paths relative to each other.

4. The method according to claim 1, further comprising shifting adjacent paths relative to each other.

5. The method according to claim 1, further comprising stretching adjacent paths relative to each other.

6. The method according to claim 1, further comprising shifting adjacent curves relative to each other in the phase.

7. The method according to claim 1, further comprising:
   defining a cut area;
   making the path larger than the cut area; and
   switching off or modifying the optical radiation on sections of the path which lies outside of the cut area such that the optical radiation does not create cuts in the transparent material outside of the cut area.

8. The method according to claim 1, further comprising forming the cuts as a skewed grid structure.

9. The method according to claim 1, further comprising forming the cuts as a grid structure by shifting the paths repeatedly in several height levels stacked along a direction of incidence of the radiation.

10. The method according to claim 1, further comprising providing between at least two height levels, an intermediate plane lying parallel to the height levels, and providing a path with which a contiguous cut is formed.

11. A method for producing control data for a femtosecond laser device which creates cuts in a transparent material in eye surgery by focusing femtosecond optical radiation, wherein the control data predetermine a curved linear path for a shift of a focus of the femtosecond optical radiation in the material, the method comprising:
   producing the control data such that the curved linear path for the shift of the focus comprises a series of sequential locations at which femtosecond laser pulses are applied thereby creating the cuts along the path and the curved linear path defines a simple or double harmonic curve when seen perpendicular to a main direction of incidence of the radiation; and
   wherein adjacent portions of the path at different depths in the transparent material are not superimposed one above another in the main direction of incidence of radiation.

12. The method according to claim 11, further comprising additionally shifting the focus this is along the main direction of incidence of the femtosecond optical radiation and relative to the main direction of incidence.

13. The method according to claim 11, further comprising rotating adjacent paths relative to each other.

14. The method according to claim 11, further comprising shifting adjacent paths relative to each other.

15. The method according to claim 11, further comprising stretching adjacent paths relative to each other.

16. The method according to claim 11, further comprising shifting adjacent curves relative to each other in the phase.

17. The method according to claim 11, further comprising defining a cut area;
   making the path larger than the cut area; and
   switching off or modifying the femtosecond optical radiation on sections of the path which lies outside of the cut area such that the optical radiation does not create cuts in the transparent material outside of the cut area.

18. The method according to claim 11, further comprising forming the cuts as a skewed grid structure.

19. The method according to claim 11, further comprising forming the cuts as a grid structure by shifting the paths repeatedly in several height levels stacked along a direction of incidence of the femtosecond optical radiation.

20. The method according to claim 11, further comprising providing between at least two height levels, an intermediate plane lying parallel to the height levels, and providing a path with which a contiguous cut is formed.

* * * * *

UNITED STATES PATENT AND TRADEMARK OFFICE
CERTIFICATE OF CORRECTION

PATENT NO.        : 10,675,183 B2
APPLICATION NO.   : 15/515473
DATED             : June 9, 2020
INVENTOR(S)       : Steffen Kahra et al.

Page 1 of 1

It is certified that error appears in the above-identified patent and that said Letters Patent is hereby corrected as shown below:

In the Specification

Column 9, Line 42, delete "10 MHz" and insert --10 MHz.--

Signed and Sealed this
Twenty-second Day of December, 2020

Andrei Iancu
*Director of the United States Patent and Trademark Office*